United States Patent [19]

Suizu et al.

[11] Patent Number: 6,111,137
[45] Date of Patent: Aug. 29, 2000

[54] PURIFICATION PROCESS OF LACTIC ACID

[75] Inventors: Hiroshi Suizu; Masanobu Ajioka, both of Kanagawa-ken, Japan

[73] Assignee: Mitsui Chemicals, Inc., Tokyo, Japan

[21] Appl. No.: 08/986,795

[22] Filed: Dec. 8, 1997

[30] Foreign Application Priority Data

Dec. 20, 1996 [JP] Japan ................................. 8-341908

[51] Int. Cl.[7] ............................ C07C 51/42; C07C 59/08
[52] U.S. Cl. .......................................... 562/580; 562/589
[58] Field of Search ...................................... 562/580, 589

[56] References Cited

U.S. PATENT DOCUMENTS 3,716,584 2/1973 Chaintron ............................... 562/589
5,310,865 5/1994 Enomoto et al. .
5,488,156 1/1996 Kulprathipanja ........................ 562/580

*Primary Examiner*—Paul J. Killos
*Attorney, Agent, or Firm*—Burns, Doane, Swecker & Mathis, L.L.P.

[57] ABSTRACT

A process for treating pyruvic acid and other impurities of lactic acid by reduction treatment of an aqueous lactic acid solution and for obtaining high quality lactic acid having a substantially no pyruvic acid content, high purity, excellent heat stability and improved smell. Further, a high molecular weight polylactic acid having low coloration and consistent quality can be prepared by dehydration polycondensation of lactic acid obtained by the reduction treatment.

2 Claims, No Drawings

PURIFICATION PROCESS OF LACTIC ACID

BACKGROUND OF THE INVENTION

1. Field of the Invention

The present invention relates to a preparation process of lactic acid. Lactic acid is widely used for preparing a soft drink, acid food, preserved food and sake in the food industry, or injection liquid and other drugs in the medicine industry. Further, recently, lactic acid is broadly used also in the chemical industry as a material of a biodegradable resin.

2. Description of the Related Art

Lactic acid is usually prepared in industry by a fermentation process and a hydrolysis process of lactonitrile or 2-chloropropionic acid. It has also been known to provide an oxidation process using nitrogen oxide of propylene, oxidation of propylene glycol or propylene oxide, and synthesis by reacting acetaldehyde with carbon monoxide. As to the separation and purification of lactic acid which is prepared by these processes, a general process is to crystallize lactic acid in the form of calcium lactate to separate soluble impurities, successively converting to lactic acid by reacting with sulfuric acid, and separating the calcium ingredient in the form of calcium sulfate crystals.

Further, activated carbon treatment, repeated recrystallization, extraction with an ion-exchange resin or organic solvent, and electrodialysis are carried out in combination in order to enhance purity of lactic acid. In another process, lactic acid is esterified with alcohol such as methanol or ethanol and is distilled to separate impurities. Lactic acid having high purity has been obtained by way of such various purification processes.

However, lactic acid obtained by these processes contains pyruvic acid, reducing sugar and other various impurities due to generation as by-products in the course of preparation or time dependent change by the action of temperature and light. As a result, it has been a problem that applications to the field requiring still higher quality are restricted in view of smell and heat stability of lactic acid.

U.S. Pat. No. 5,310,865 has disclosed a preparation process of high molecular weight polyhydroxycarboxylic acid by direct dehydration condensation of lactic acid or other hydroxycarboxylic acid and a preparation process of a film, filament and molded articles which contain said polyhydroxycarboxylic acid and have an excellent strength.

In the preparation of polylactic acid according to the above technique lactic acid having a relatively high quality is used in order to obtain a high molecular weight polymer having practical strength. However, in such cases, resulting polylactic acid is sometimes colored due to the difference in species or lot of lactic acid used and cannot provide a consistent property.

As to the purification process of trace impurities contained in lactic acid, Japanese Laid-Open Patent SHO 56-65841 has disclosed a process for purifying lactic acid by adding water to an aqueous lactic acid solution and successively conducting distillation. It has been described that the smell of lactic acid can also be improved as a result of removing aldehyde contained in an amount of several tens of ppm and distilling off trace impurities such as methanol and acetic acid at the same time.

However, the process requires addition of a large amount of water for carrying out purification and the cost of concentration and distillation rises. The distilled water has a problem of waste water disposal. Additionally, impurities which are difficult to efficiently remove by the process still remain in lactic acid. For example, pyruvic acid is difficult to remove and thus the process has not always been a satisfactory purification process.

Consequently, the object of the invention is to provide a novel purification process of high quality lactic acid which is free from pyruvic acid and has improved smell and heat stability by removing with a simple procedure pyruvic acid and other trace impurities contained in lactic acid.

SUMMARY OF THE INVENTION

As a result of an intensive investigation in view of the above subjects, the present inventors have found that high quality lactic acid which contains no pyruvic acid and has extremely improved smell and heat stability can be obtained by simple reduction treatment including a catalytic reduction process with hydrogen or hydrogen containing gas or a reduction process with a metal. Thus the present invention has been completed.

Polylactic acid having scarce coloration and consistent quality can be obtained by using thus reduction-treated lactic acid as a material of the polymer.

That is, various aspects of the invention are characterized by the subjects [1]–[9] described below.

[1] A purification process of lactic acid comprising subjecting an aqueous lactic acid solution to reduction treatment.

[2] The purification process of lactic acid according to [1], wherein purified lactic acid has APHA of less than 50 after heating at 180° C. for 2 hours.

[3] The purification process of lactic acid according to [1], wherein the reduction treatment is a catalytic reduction treatment.

[4] The purification process of lactic acid according to [3], wherein the reduction treatment is carried out in the presence of one or more reduction catalyst selected from the group consisting of palladium, platinum and a compound of these metals.

[5] The purification process of lactic acid according to [1], wherein a metal is used as a reducing agent in the reduction treatment.

[6] The purification process of lactic acid according to [5], wherein the metal used as the reducing agent is one or more metal selected from the group consisting of metallic iron, metallic tin and metallic zinc.

[7] Lactic acid purified according to [1].

[8] Lactic acid containing less than 5 ppm of pyruvic acid and used for polymerization.

[9] Polylactic acid obtained by using lactic acid of claim 8 as a raw material and having an yellowness degree (YI value) of 3.0 or less.

DETAILED DESCRIPTION OF THE PREFERRED EMBODIMENTS

The invention will be illustrated in detail hereinafter.

The process of the invention can be applied to lactic acid prepared by any processes and is particularly suited to lactic acid prepared by a fermentation process.

Lactic acid which can be used in the invention includes a lactic acid monomer and, additionally, lactic acid oligomer (lactic acid condensate having a number average molecular weight of 300 or less) and a mixture of these compounds. The lactic acid oligomer having a number average molecular weight exceeding 300 generally leads to high solution viscosity and thus reduction procedures become difficult.

Further, it becomes unfavorably difficult after reduction treatment to remove the reduction catalyst used for the reaction or the unreacted metal used for the reducing agent.

Lactic acid used for the purification process of the invention is usually in the state of an aqueous solution.

No particular limitation is imposed upon the lactic acid concentration in the aqueous lactic acid solution. An aqueous lactic acid solution having an arbitrary concentration can be used, and generally, a solution having a concentration of 20 wt % or more is preferably used.

Lactic acid to be used for the process of the invention is preferably incorporated with water or concentrated in advance in order to control concentration of the aqueous lactic acid solution so as to accommodate the object for use of lactic acid which is purified by the process of the invention.

The reduction treatment is carried out by using a metal, metal salt, metal hydride, metal hydride complex or phosphorus compound, and by way of catalytic reduction or electrolytic reduction as described in Shin Jikkenkagaku Koza, vol 15, Oxidation and Reduction [II], published by Maruzen (1997). However, no particular restriction is imposed upon the reduction treatment process so long as the process has substantially no effect on lactic acid and/or water, and can reduce contaminated oxides in the aqueous lactic acid solution without substantial inhibition by lactic acid and/or water.

Consequently, it is unfavorable to carry out the reduction treatment by using metallic sodium, lithium aluminum hydride, boron and other compounds having high reactivity with water. Sodium boron hydride, hydrazine, diimide and other compounds having a high reactivity with lactic acid cannot be utilized for the reduction treatment.

Any process for the reduction treatment can be used in the invention so long as, as mentioned above, giving substantially no effect on lactic acid and/or water, or having substantially no inhibition by lactic acid and/or water. In view of convenience to reduction procedures and post treatment and availability of a reagent, preferred reduction treatment is catalytic reduction and use of metallic iron, metallic tin, metallic zinc and other metals as a reducing agent.

When catalytic reduction is used in the reduction treatment of the invention, the term "catalytic reduction" refers to a species of reduction process which uses hydrogen in the presence of a suitable catalyst and reduces reducible impurities which are present in lactic acid, for example, pyruvic acid and reducing sugar.

The catalytic reduction in the invention includes a process described in Shin Jikkenkagaku Koza, vol 15, Oxidation and Reduction [II], page 333–448 (published by Maruzen, 1997).

In the process of the invention, catalytic reduction is usually carried out by adding a catalyst to an aqueous lactic acid solution and treating with hydrogen or hydrogen containing gas consisting of hydrogen and an inert gas such as nitrogen and argon. The end point of the reaction is determined by measuring termination of hydrogen gas absorption.

No particular restriction is imposed upon the catalyst for use in the catalytic reduction of the invention so long as the catalyst does not react with lactic acid. Exemplary catalysts which can be used for the invention include, for example, palladium, platinum, rhodium, ruthenium and copper. These catalysts can be used singly or as a mixture.

These catalysts can also be used in the state of metal. However, they are usually applied by supporting on the surface of carriers such as carbon, barium sulfate, silica gel and alumina. Catalysts which can be suitably used are a platinum catalyst supported on activated carbon or alumina.

The amount of these catalysts is in the range of 0.01 to 30 wt % as metal for the raw material, the aqueous lactic acid solution, and usually used by supporting on a carrier in the range of 0.01 to 5 wt %.

The temperature of catalytic reduction in the invention is generally in the range of 0 to 150° C., preferably in the range of 10 to 100° C.

The reaction pressure in the catalytic reduction process of the invention use usually from atmospheric pressure to 50 kg/cm$^2$.

After finishing the reduction treatment, the reaction system is replaced by nitrogen or other inert gas, and lactic acid and the catalyst are separated.

No particular restriction is imposed upon the separation method of the aqueous lactic acid solution from the catalyst.

The separation can be carried out by simple procedures, for example, the catalyst is filtered, alternatively the aqueous lactic acid solution containing the catalyst is allowed to stand or subjected to centrifugal sedimentation and successively the resulting supernatant liquid is decanted.

The separated catalyst is recovered and can be used again.

When the reduction treatment in the invention is carried out by using a metal as a reducing agent, the metal is used under acid conditions and reduces reducible impurities other than lactic acid, for example, pyruvic acid and reducing sugar. In the reduction treatment, the reaction velocity can be increased by adding mineral acids such as hydrochloric acid, sulfuric acid and nitric acid at the same time to enhance acidity of the reaction system. However, acidity of lactic acid itself is usually satisfactory to progress the reducing reaction.

Metals as the reducing agent in the invention are preferably metallic iron, metallic tin and metallic zinc.

The amount of metals used as the reducing agent in the invention is usually a satisfactory amount or a large excess amount for reducing other impurities contaminated in lactic acid.

The reaction temperature is generally in the range of 0 to 150° C., preferably in the range of 10 to 100° C.

Embodiments for practicing the process for using the metal as a reducing agent in the invention include procedures for adding metal powder to the aqueous lactic acid solution, stirring the mixture at the prescribed temperature to carry out reduction, and successively filtering an unreacted metal, or methods for separation by allowing to stand or centrifugally settling the aqueous lactic acid solution containing the unreacted metal and subsequent decantation. Other embodiments for practice include procedures for charging a granular reducing agent into a column or other packed chambers and carrying out reduction while passing the aqueous lactic acid solution through the column.

The end point of the reaction is inspected by HPLC. Pyruvic acid and other impurities in lactic acid are analyzed in the course of reaction and the reduction procedure is terminated when the impurities are no longer detected.

The excess unreacted metal remaining can be repeatedly used. The procedures can be carried out batch wise, semi-batch wise and continuously.

After finishing reduction by using the metal as a reducing agent, the aqueous lactic acid solution, that is, the reaction mass, contains a reacted metal ingredient and the added mineral acid ingredient, when used. No particular restriction is imposed upon the method for separating and removing these ingredients used for reducing the impurities in lactic acid. The methods which can be practiced are, for example, treatment of the metallic ingredient with an H-type strongly acidic ion exchange resin and treatment of the mineral acid ingredient with an OH-type or lactic acid type strongly basic anion exchange resin.

Alternatively, the treatment method which uses these metals as a reducing agent in the invention can be carried out in combination with other known purification methods, for example, a method for reacting lactic acid with alcohol, separating resultant lactate ester by distillation, and successively hydrolyzing lactate ester to obtain pure lactic acid.

The reduction treatment of lactic acid in the invention reduces pyruvic acid contained in lactic acid and at the same time reduces aldehyde compounds and other impurities. As a result, high quality lactic acid purified by the reduction treatment of the invention is substantially free from pyruvic acid, has an excellent heat stability, and is remarkably improved in smell.

Specifically, marketed lactic acid contains several tens to several hundreds ppm of pyruvic acid, more than 1000 ppm in some species of lactic acid. However, after reduction treatment of the invention, pyruvic acid cannot be detected by HPLC analysis having a detection limit of 5 ppm.

Further, a scarcely colored polylactic acid can be prepared by direct dehydration polycondensation of a lactic acid raw material purified by the process of the invention.

The process for preparing a polymer from the lactic acid raw material has already been known. For example, U.S. Pat. No. 5,310,865 has disclosed a preparation process of aliphatic polyhydroxycarboxylic acid which comprises carrying out a heat dehydration polycondensation reaction of aliphatic hydroxycarboxylic acid in an organic solvent in the presence of a catalyst, while distilling out generated water from the reaction system together with the organic solvent and charging into the reaction system an additional organic solvent having a moisture content less than the moisture content of the distilled organic solvent.

When polylactic acid is prepared from lactic acid raw material according to the process, a relatively high quality lactic acid is used in order to obtain a high molecular weight lactic acid polymer having a weight average molecular weight of 50,000 or more and practical strength.

However, some species of lactic acid contain a small amount of contaminated pyruvic acid even though these species can provide a high molecular weight polylactic acid. As a result, the resulting polylactic acid leads to coloration and the degree of coloration varies from lot to lot of lactic acid, even though the same grade of lactic acid is used. It has thus been difficult to consistently prepare the lactic acid polymer having a constant quality.

On the other hand, the use of lactic acid which has been purified by the reduction treatment of the invention and contains substantially no pyruvic acid can consistently provide a high molecular weight polymer having a low coloration, that is, an Yellow Index of 3.0 or less by carrying out a dehydration polycondensation reaction according to the process disclosed in U.S. Pat. No. 5,310,865.

EXAMPLES

The present invention will hereinafter be illustrated further in detail by way of examples. However, descriptions in these examples are included merely to aid in the understanding of the invention and are not to be construed to limit the scope of the invention.

Following methods were used for the analysis and evaluation in these examples.

Pyruvic acid determination was described as a representative example of the analysis for lactic acid impurities. However, the lactic acid impurities which can be reduced by the treatment of the invention are not limited to pyruvic acid.

These examples were described on the weight basis, unless otherwise noted.

(1) Analysis of Impurities in Lactic Acid (Pyruvic acid)

Pyruvic acid was determined by HPLC under following conditions. The detection limit of pyruvic acid was 5 ppm.

Analytical conditions in HPLC

Column: YMC A-312 ODS (6×150 mm)

Eluent: acetonitrile/water=5/95 (pH=2.0/phosphoric acid)

Flow rate: 1.0 mol/min

Detection: $\lambda$=225 nm (2) Heat Stability Test of Lactic Acid

Heat stability of lactic acid was evaluated by measuring coloration of lactic acid with an APHA method after heating at 180° C. for 2 hours.

The standard color solution used for the APHA method was prepared by dissolving 1.246 g of potassium chloroplatinate ($K_2PtCl_6$) (500 mg as platinum) and 1.0 g of cobalt chloride ($CoCl_2.6H_2O$) in 100 ml of hydrochloric acid and diluting the resulting solution with water to 1 liter. The color solution thus obtained designated color number 500. Any reagents used were special grades and water used was distilled water. Color numbers 100, 50, 20, and 10 were prepared from the solution of a color number 500 by individually diluting with distilled water 5, 10, 25 and 50 times. These solutions were respectively charged into a test tube having specified dimensions (diameter 3 cm×length 20 cm). The test sample was also charged into a test tube having the same dimensions and composed its color with a standard color solution by visual observation from the upper surface of the charged solution. The coloration was indicated by the number of a standard color solution having the same feeling of color.

(3) Weight Average Molecular Weight

Weight average molecular weight (MW) of polylactic acid obtained was measured by gel permeation chromatography at a column temperature of 40° C. in a chloroform solvent. Polystyrene was used as a reference.

(4) Yellowness Degree (YI value)

A plate specimen having a thickness of 2 mm was prepared from polylactic acid obtained. The yellowness of the specimen was measured with a SM color computer : Model, SM-6-IS-2B, manufactured by Suga Shikenki Co., in accordance with JIS K-7103.

Example 1

To a sealed type reducing reactor equipped with a stirrer and thermometer, 185 g of marketed L-lactic acid having a concentration of 88% and 3.08 g of a 5% palladium alumina catalyst manufactured by NE Chemcat Co. were charged and the reaction system was substituted with nitrogen. After substituting the reaction system with hydrogen, catalytic reduction treatment was carried out with violent stirring at 25° C. under atmospheric pressure. During stirring for 40 minutes, 45 ml of hydrogen was absorbed. Thereafter no additional absorption was observed and thus the reaction was terminated after stirring for an hour. The reaction system was substituted with nitrogen and successively separated the catalyst by filtration. The reduction-treated lactic acid was thus obtained.

Pyruvic acid in lactic acid was analyzed. Pyruvic acid content was 480 ppm before reduction treatment, whereas no pyruvic acid was detected after reduction treatment. Further, lactic acid before reduction treatment had nasty smell which differed from the essential odor of lactic acid. However, no nasty smell was detected from the lactic acid after reduction treatment.

Lactic acid before reduction treatment had APHA of 80 after heating at 180° C. for 2 hours. On the other hand, lactic acid after reduction treatment had APHA of 30 under the same conditions. Thus, the grade of coloration was also improved.

Example 2

The same procedures as Example 1 were carried out except that the catalyst for use was changed to 1.16 g of a 50% water containing 5% palladium carbon catalyst (manufactured by NE Chemcat Co.) and catalytic reduction treatment was carried out at 60° C. During stirring for 30 minutes, 45 ml of hydrogen was absorbed and additional absorption was not observed. Thus, the reaction was terminated after stirring for an hour. The reaction system was substituted with nitrogen and the catalyst was separated by filtration and subjected to reduction treatment to obtain purified lactic acid.

Pyruvic acid content of lactic acid was analyzed. Before the reduction treatment, pyruvic acid content was 480 ppm. However, no pyruvic acid was detected after the reduction treatment. Further, nasty smell which differed from the essential odor of lactic acid was perceived on lactic acid before the reduction treatment, whereas no nasty smell was detected from the lactic acid after the reduction treatment.

Lactic acid obtained by the reduction treatment was heated at 180° C. for 2 hours. Resulting lactic acid had APHA of 20.

Example 3

After adding 5 g of iron powder to 200 g of marketed L-lactic acid (88% concentration) which was used in Example 1, the reaction mixture was stirred at 70° C. stirring was continued until no pyruvic acid was detected by HPLC, and successively unreacted iron powder was separated by filtration from an aqueous lactic acid solution. After cooling the aqueous lactic acid solution to room temperature, the dissolved iron compound was removed by passing the solution through an ion exchange resin column (DIAION, SK-1B) which was adjusted to H-type.

Lactic acid thus obtained was heated at 180° C. for 2 hours. Resulting lactic acid had APHA of 20.

Lactic acid before the reduction treatment had nasty smell which differed from the essential odor of lactic acid. On the other hand, no nasty smell was detected from the lactic acid after the treatment.

Example 4

After adding 5 g of tin powder to 200 g of marketed L-lactic acid (88% concentration) which was used in Example 1, the reaction mixture was stirred at 70° C. until no pyruvic acid was detected by HPLC. Thereafter, unreacted tin powder was separated by filtration from an aqueous lactic acid solution. After cooling the aqueous lactic acid solution to room temperature, the dissolved tin compound was removed by passing the solution through an ion exchange resin column(DIAION, SK-1B) which was adjusted to H-type.

Lactic acid before the reduction treatment had nasty smell which differed from the essential odor of lactic acid. On the other hand, no nasty smell was detected from the lactic acid after the treatment.

Example 5

To a 500 ml round bottomed flask, 103.2 g of 88% L-lactic acid which was obtained by the reduction treatment in Example 2 and 0.43 g of stannous oxide as a polymerization catalyst were charged, and heated with stirring at 140° C./100 mmHg for 3 hours while distilling water out of the reaction system. Thereafter, a Dean Stark trap was charged with 72 g of o-dichlorobenzene and mounted on the flask. Further, 72 g of O-dichlorobenzene was added to the reaction mass and azeotropic dehydration was carried out at 140° C./270 mmHg for 4 hours. Dean Stark trap was dismantled and a tube which was packed with 30 g of molecular sieve 3A and filled with O-dichlorobenzene was equipped on the flask so as to return the reflux distilled solvent to the reaction system again by way of the molecular sieve layer. The reaction was carried out by heat stirring at 140° C./270 mmHg for 24 hours while preventing contamination of water into the reaction system.

The reaction mass was cooled to 30° C., incorporated with 800 ml of a 0.7% hydrochloric acid/isopropyl alcohol solution, stirred for an hour, and suction-filtered to remove the catalyst. Successively, the filter cake was stirred in 600 ml of isopropyl alcohol and suction filtered. The procedure was repeated until neutral filtrate was obtained.

The filter cake thus obtained was dried at 60° C. in hot air to obtain 59.6 g (82% yield) of polylactic acid.

Polylactic acid thus obtained had a weight average molecular weight of 143,000 and a yellowness degree (YI value) of 1.5.

Example 6

Polymerization was carried out by the same procedures as described in Example 5 except that 88% L-lactic acid obtained by the reduction treatment in Example 3 was used. Polylactic acid thus obtained was 60.0 g (83% yield) and had a weight average molecular weight of 145,000 and yellowness degree(YI value) of 1.3.

Comparative Example 1

To 200 g of marketed L-lactic acid which was used in Example 1 and had a concentration of 88%, 200 g of distilled water was added and concentrated to obtain a whole weight of 200 g at 50 to 55° C. under reduced pressure of 90 to 50 mmHg.

Lactic acid thus treated had no nasty smell. However, pyruvic acid content was 420 ppm after the treatment, that is, pyruvic acid was merely slightly decreased from the original content. Lactic acid thus obtained had APHA of 50 after heating at 180° C. for 2 hours.

Polymerization was carried out by the same procedures as described in Example 5 using 88% L-lactic acid thus obtained.

Polylactic acid thus obtained was 59.5 g (82% yield) and had a weight average molecular weight of 145,000 and yellowness degree(YI value) of 4.3.

Comparative Example 2

Marketed 88% L-lactic acid used in Example 1 was polymerized as intact without reduction treatment by carrying out the same procedures as described in Example 5.

Polylactic acid thus obtained was 58.5 g (81% yield) and had a weight average molecular weight of 143,000 and yellowness degree(YI value) of 4.8.

Table 1 illustrates relationships of the weight average molecular weight and yellowness degree (YI value) of polylactic acid obtained by polymerization in Example 5 and 6, and Comparative Example 1 and 2, to a pyruvic acid content of the lactic acid raw material and grade of coloration (APHA) after heating at 180° C. for 2 hours.

TABLE 1

|  | Lactic acid raw material | | Polylactic acid obtained | |
|---|---|---|---|---|
|  | Pyruvic acid [ppm] | APHA after heating test | Weight average molecular weight | Yellowness degree (YI value) |
| Example 5 | not detected | 20 | 143,000 | 1.5 |
| Example 6 | not detected | 20 | 145,000 | 1.3 |
| Comparative Example 1 | 420 | 50 | 145,000 | 4.3 |
| Comparative Example 2 | 480 | 70 | 143,000 | 4.8 |

What is claimed is:

1. A process for preparing purified lactic acid comprising preparing lactic acid by fermentation which contains pyruvic acid as a by-product and subjecting an aqueous solution of the lactic acid and pyruvic acid to reduction treatment under conditions sufficient to reduce pyruvic acid, wherein a metal is used as a reducing agent in the reduction treatment whereby the purified lactic acid exhibits an APHA of less than 50 when heated at 180° C. for 2 hours.

2. A process for preparing purified lactic acid comprising preparing lactic acid by fermentation which contains pyruvic acid as a by-product and subjecting an aqueous solution of the lactic acid and pyruvic acid to reduction treatment under conditions sufficient to reduce pyruvic acid w here in the reduction treatment is catalytic reduction in the presence of one or more reduction catalysts selected from the group consisting of palladium, platinum and a compound of the same whereby the purified lactic acid exhibits an APHA of less than 50 when heated at 180° C. for 2 hours.

* * * * *